United States Patent [19]
Alberti et al.

[11] Patent Number: 5,453,172
[45] Date of Patent: * Sep. 26, 1995

[54] SOLID-STATE SENSOR FOR DETERMINING THE CONCENTRATION OF A GAS WITH A SOLID-STATE REFERENCE ELECTRODE

[75] Inventors: Giulio Alberti; Roberto Palombari, both of Perugia, Italy

[73] Assignees: Eniricerche S.p.A., Milan; Snam S.p.A., San Donato Milanese, both of Italy

[*] Notice: The portion of the term of this patent subsequent to Jul. 28, 2009 has been disclaimed.

[21] Appl. No.: 879,122

[22] Filed: May 5, 1992

Related U.S. Application Data

[63] Continuation of Ser. No. 573,269, Aug. 27, 1990, abandoned, which is a continuation of Ser. No. 311,943, Feb. 17, 1989, abandoned.

[30] Foreign Application Priority Data

Feb. 22, 1988 [IT] Italy ................................ 19477A/88

[51] Int. Cl.$^6$ .................................................. G01N 27/26
[52] U.S. Cl. ........................ 204/421; 204/424; 204/426
[58] Field of Search ................................ 204/421, 424, 204/426; 429/191, 192, 193

[56] References Cited

U.S. PATENT DOCUMENTS

| | | | |
|---|---|---|---|
| 3,218,242 | 11/1965 | Capuano | 204/1 |
| 3,565,769 | 2/1971 | Holden et al. | 204/1 |
| 3,727,058 | 4/1973 | Schrey | 204/1 T |
| 4,179,491 | 12/1979 | Howe et al. | 429/191 X |
| 4,240,879 | 12/1980 | Dobson | 204/1 T |
| 4,513,069 | 4/1985 | Kreuer et al. | 429/192 |
| 4,661,211 | 4/1987 | Petty-Weeks | 204/1 T |
| 4,664,757 | 5/1987 | Zupancic et al. | 204/1 T |
| 4,689,122 | 8/1987 | Polak et al. | 204/1 T |
| 4,718,991 | 1/1988 | Yamazoe et al. | 204/1 T |
| 5,133,857 | 7/1992 | Alberti et al. | 204/425 |

FOREIGN PATENT DOCUMENTS

| | | | |
|---|---|---|---|
| 0231766 | 8/1987 | European Pat. Off. . | |
| 50458 | 3/1983 | Japan | 204/421 |
| 2128751 | 5/1984 | United Kingdom . | |

OTHER PUBLICATIONS

A. J. Polak et al., Sensors and Actuators, 9, 1–7, (1986).
Sensors and Actuators, vol. 9, No. 1, Feb. 1986, pp. 1–7; A. J. Polak et al: "Applications of Novel Proton–Conducting polymers of Hydrogen Sensing".
Analytical Chemistry Symposia Series, vol. 17, "Chemical Sensors", Proceedings of the International Meeting on Chemical Sensors, Fukuoka, 19th–22nd Sep. 1983, pp. 239–244; G. Velasco et al: "New Protonic Materials for Hydrogen Sensors".
1985 International Conference on Solid–State and Actuators, 1985, pp. 340–343; No. Yamazoe et al: "Development of Proton Conductors Gas Sensor". (no month).
S. B. Lyon et al, "Hydrogen Measurements Using Hydrogen Uranyl Phosphate Tetrahydrate", Solid State 9 & 10 (1983) pp. 1295–1298, North–Holland Publishing Company.
"Instantaneous Determination of Hydrogen Content in Molten Aluminum and its Alloys"by R. Gee and D. J. Fray, Metallurgical Transactions vol. 9B 9/78 p. 427–430, 1978 American Society for Metals and The Metallurgical Society of Aime. (no month).
"Impurity Monitoring in Liquid Sodium Systems by Electrochemical Oxygen and Hydrogen Monitors"by George J. Licina et al.—Material Behavior and Physical Chemistry in Liquid Metal Systems, [Proc. Conf.], meeting Date 1981, p. 297–307. (no month).

*Primary Examiner*—Kathryn Gorgos
*Assistant Examiner*—Arun S. Phasge
*Attorney, Agent, or Firm*—Oblon, Spivak, McClelland, Maier & Neustadt

[57] ABSTRACT

A sensor in completely solid state for determining the concentration of a gas, in particular of hydrogen, is disclosed, which is essentially constituted by electrodes separated by a protonic conductor in the solid state, in which the solid-state reference electrode is constituted by a metal hydride, or a metal-alloy hydride.

4 Claims, 4 Drawing Sheets

SOLID-STATE SENSOR FOR DETERMINING THE CONCENTRATION OF A GAS WITH A SOLID-STATE REFERENCE ELECTRODE

This application is a continuation of application Ser. No. 07/573,269 filed Aug. 27, 1990, now abandoned, which is a continuation of application Ser. No. 07/311,943, filed Feb. 17, 1989, now abandoned.

The present invention relates to a sensor in completely solid state for determining the concentration of a gas, in particular of hydrogen.

FIELD OF THE INVENTION

In many processes deserving interest at a commercial level, not only the presence of determined gases should be detected, but it is important as well to have available a simple method, which makes it possible such gases to be continuously and quantitatively monitored in the atmosphere or in the reaction environment.

DISCUSSION OF THE BACKGROUND

Some examples relevant to the detection of hydrogen are:

—In case hydrogen leaks occur in closed rooms, such leaks should be quickly detected, in order to prevent any explosion risks.

—Many metals and their alloys (for example, steels, titanium, zirconium, and so forth) react with hydrogen to yield hydrides, with their mechanical characteristics being consequently impaired.

—In many corrosion phenomena, hydrogen generated: therefore, the presence of hydrogen can be indicative of the fact that a corrosion process is taking place (this is useful in particular in order to check parts which are not easily accessible in case of a direct inspection).

—The continuous monitoring of hydrogen in reactions producing or consuming such a gas can be useful in order to control the same reactions for the best.

Prior to 1980, hydrogen was essentially detected by means of polarographic techniques, as disclosed by K. Barthlett, J. V. Dobson, E. Easthman in Chimica Acta 108, 189 (1980), but in the past years a strong trend arose in the art, to replace such a method with simpler and less cumbersome electrochemical devices, such as sensors based on solid-state electrolytes.

In case of hydrogen, such sensors use a protonic-conduction solid, which separates two compartments containing different hydrogen partial pressures.

At the platinum electrodes, installed on both mutually opposite faces of the protonic conductor, an e.m.f. is generated, the value of which is given by the Nernst equation.

For not very high pressures, such an equation can be written as follows:

$$E = RT/nF \, Ln \, P_{H2}/P_{H2(ref)} \qquad (1)$$

wherein:

R is the constant of gases (8.34 J.gmol$^{-1}$. K$^{-1}$),

F is the Faraday constant (96,500 Coulombs),

T is the absolute temperature as degrees Kelvin and n is the number of electrons involved in the process.

In the specific case of hydrogen, n is 2 (in that the process is:

$$H_2 \rightleftharpoons 2H^+ + 2e).$$

Going to decimal logarithms, we have, at 25° C.:

$$E = .0296 \, log \, P_{H2}/P_{H2(ref)} \qquad (2)$$

If the reference partial pressure is known, the unknown $P_{H2}$ pressure can be obtained from a potentiometric measurement of E.

To date, various inorganic solid substances are known, which are endowed with a relatively high protonic conductivity at room temperature, such as, e.g.: uranyl hydrogen phosphate, antimonic acid, phosphomolybdic acid, zirconium hydrogen phosphate and dizirconium triphosphate in hydrogen form.

All these protonic conductors are therefore endowed with applicative potentialities in hydrogen sensors. Also some organic polymers, such as Nafion in hydrogen form, can be used as protonic conductors, such as described by J. Jensen in "Solid State Protonic Conductors for Fuel Cells and Sensors" (page 1, Editors: Godehough J. B. Jensen, Poitier A., Odense University Press, 1985).

Some of such solids have actually given rather good results in the manufacturing of sensors for hydrogen gas (see, e.g., Miura N., Karo N. Yamatoe and Jeiyama T., Proc. Int. Meet. Chem. Sensors, Fukuoka, page 233, 1983).

A further simplification is obtained in the sensor if a reference electrode in the solid state is used, thus a completely solid-state sensor being accomplished.

When a solid-state reference is used, the equation (2) can be advantageously written as:

$$E = constant - .0296 \, Log \, P_{H2}$$

wherein the value of the constant depends on the reference electrode used.

For example, a reference in the solid state reported in the relevant technical literature is constituted by a silver foil.

BRIEF DESCRIPTION OF THE DRAWINGS

A more complete appreciation of the invention and many of the attendant advantages thereof will be readily obtained by reference to the following detailed description when considered in connection with the accompanying drawings, wherein.

DETAILED DESCRIPTION OF THE PREFERRED EMBODIMENTS

Figure 1:
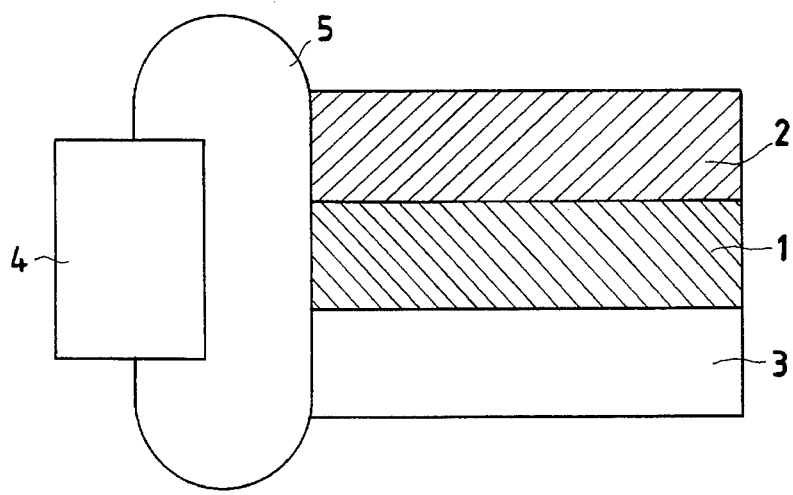
In FIG. 1, the following elements are indicated; 1. the protonic conductor in the solid state; 2. the catalyzing electrode; 3. the reference electrode in the solid state; 4. the instrument for e.m.f. measurement; 5. the compartment inside which the hydrogen to be determined is contained.

The present Applicant has found that, in the presence of high hydrogen partial pressures, a total reduction of Ag$^+$ in the protonic conductor may take place. The present Applicant has found that such a drawback can be prevented from occurring by using, contrarily to as reported in the technical literature by Lyon S. B. and Fray J. D. (Solid-State Ionics, 9–10, 1295/1983), electrodes which consist of hydrides of a metal or of hydrides of a metal alloy placed into contact with the protonic conductor, such as, e.g., interstitial titanium hydride ($TiH_x$) or interstitial zirconium hydride ($ZrH_x$):

The solid-state sensor for determining the concentration of a gas, in particular of hydrogen, which is the object of the present invention, is essentially constituted by electrodes separated by a solid-state protonic conductor, wherein the solid-state reference electrode is constituted by a metal hydride selected from the group consisting of titanium and zirconium hydrides..

Those gases can be determined, which are capable of altering the electrochemical potential of protons at the interface between the protonic conductor and the monitored gas.

As the protonic conductor, those known from the technical literature, such as, e.g., uranyl hydrogen phosphate, antimonic acid, phosphomolybdic acid, zirconium hydrogen phosphate and dizirconium triphosphate in hydrogen form, can be used.

Zirconium phosphate can preferably be in film form, or in a membrane form.

In the U.S. patent application No. 485,342 a process is disclosed for obtaining colloidal dispersions of zirconium phosphate, by means of which either coating various solids with a thin and compact film of such a protonic conductor; or obtaining zirconium phosphate in the form of very thin membranes, results possible.

A small amount of the aqueous dispersion of colloidal zirconium phosphate can be directly stratified on the reference electrode. After the evaporation of water, the electrode is thus coated by an adhering, thin and compact film of zirconium phosphate. The sensor can be subsequently finished by depositing on said film, by sputtering, a thin platinum layer. By such a route, a total sensor thickness lower than 1 mm can be obtained. By having available a suitable technology, such a method is particularly well suited for accomplishing microsensors for hydrogen gas in completely solid state.

As the catalysing electrodes, those known from the technical literature can be used; among them, platinum and palladium may be cited for exemplifying purposes.

The preparation of the titanium hydride or zirconium hydride reference electrode can be carried out, e.g., by heating a thin sheet of titanium or zirconium (of from 0.25 mm to 1 mm of thickness) at a temperature comprised within the range of from 400° to 700° C., for a time comprised within the range of from 2 to 10 hours, in the presence of hydrogen gas.

The preparation of a sensor in completely solid state for hydrogen gas, with a solid-state titanium-hydride or zirconium-hydride reference electrode, and a protonic conductor constituted by zirconium hydrogen phopshate in film form, or in membrane form, can be carried out, for example, by means of the following operating steps:

a) the titanium-hydride or zirconium-hydride reference electrode is prepared;

b) the aqueous dispersion of colloidal zirconium phosphate is prepared;

c) the reference elect rode is coated with zirconium phosphate in film form (or with a pre-formed membrane of zirconium phosphate);

d) on the free face of the zirconium phosphate in film form (or of the pre-formed zirconium phosphate membrane) a thin layer of platinum (or of palladium) is deposited.

a) Preparation of the Titanium-Hydride or Zirconium-Hydride Reference Electrodes Said preparation has already been disclosed in the foregoing pages, b) Preparation of the Dispersion of Colloidal Zirconium Phosphate Zirconium hydrogen phosphate monohydrate, having a layer structure of $\alpha$ type, $\alpha\text{-}Zr(HPO_4)_2 \cdot H_2O$ (preferably prepared by means of the method of precipitation in the presence of hydrofluoric acid, as described by Alberti G. and Torraca E. in J. Inorg. Nucl. Chem., 30, 317 (1969), was intercalated up to 50% of its total capacity with propylamine. With strong stirring, in such a way a colloidal dispersion of lamellar particles of zirconium phosphate in propyl-ammonium form can be obtained. Dispersions containing 1 gram of zirconium phosphate in 200 ml of water do not appreciably settle, and therefore can be easily maintained at room temperature for long time periods (even for some months) after being prepared. In order to obtain again zirconium phosphate in hydrogen form, a mineral acid should be added (generally 0.1M HCl, in an amount of 25 ml per each 100 ml of dispersion). At the end of the addition, carried out with strong stirring, zirconium phosphate still remains in the dispersed state. However, such dispersions tend to settle, even if slowly, and can be easily separated from the solution (e.g., by means of centrifugation at 2,000 revolutions per minute). Zirconium phosphate is then dispersed again in distilled water, and the treatment with HCL is repeated, until propyl-ammonium chlorides completely removed.

c) Coating of the Titanium-Hydride or Zirconium-Hydride Reference Electrode with Zirconium Phosphate —Coating with Zirconium Phosphate in Film Form A suspension of colloidal zirconium phosphate in hydrogen form, prepared according to as disclosed under (b), is evenly sprayed (e.g., by means of a sprayer device for use in chromatography) onto a sheet of titanium hydride or zirconium hydride. After drying in air, the sheet results to be coated with an adhering and compact film of zirconium phosphate. According to an alternative route, a slab of the material to be coated, is placed on the bottom of a Petri dish having a diameter slightly larger than said slab. Above the slab a layer of a few millimiters of colloidal suspension of zirconium phosphate is deposited. After water evaporation, the slab remains coated with an adhering film of zirconium phosphate.

For the preparation of single, small-size electrodes, on the slabs of the reference material a drop of suspension is deposited and is allowed to dry. This treatment can be repeated a plurality of times, until a film having the desired thickness is obtained.

Coating with a Previously Prepared Membrane of Zirconium Phosphate

The dispersion of zirconium phosphate in distilled water is slowly filtered through a flat filter of a porous plastic material, in its turn placed above a paper filter. After the end of the filtration the filter, bearing the zirconium phosphate stratified on it, is dried. After such a drying, from the filter the deposited zirconium phosphate can be easily separated as a compact membrane, endowed with a certain flexibility; the thickness of said membrane is a function of the amount of suspension used, of the concentration of suspended solids in it, and of the surface area of the filter.

d) Deposition of a Platinum Layer on Zirconium Phosphate

A good method used by the present Applicant in order to obtain an active enough platinum surface consists in carrying out a Pt sputtering directly on the film layer, or on the membrane of zirconium hydrogen phosphate. By using a Balzers Union (SCD040) device, the conditions most frequently used by the present Applicant are: electrical current intensity 15 mA; argon pressure 0.05–0.1 mbar; sputtering time 10–20 minutes.

Another method used by the present Applicant consists in adding platinum black to a colloidal dispersion of zirconium phosphate (10–20 parts of platinum black per each part of zirconium phosphate), Platinum black is emulsified by stirring. A few droplets of such an emulsion is deposited on the membrane of zirconium phosphate, and is allowed to dry.

The sensors according to the present invention can be schematized as shown in FIG. 1.

In FIG. 1, by the following reference numerals the following elements are indicated:

1. the protonic conductor in the solid state;
2. the catalysing electrode;
3. the reference electrode in the solid state;
4. the instrument for e.m.f. measurement;
5. the compartment inside which the hydrogen to be determined is contained.

Some examples are given now, which have the purpose of better illustrating the present invention, it being understood that the same invention should not be regarded as being limited by them or to them.

EXAMPLE 1

Figure 2:
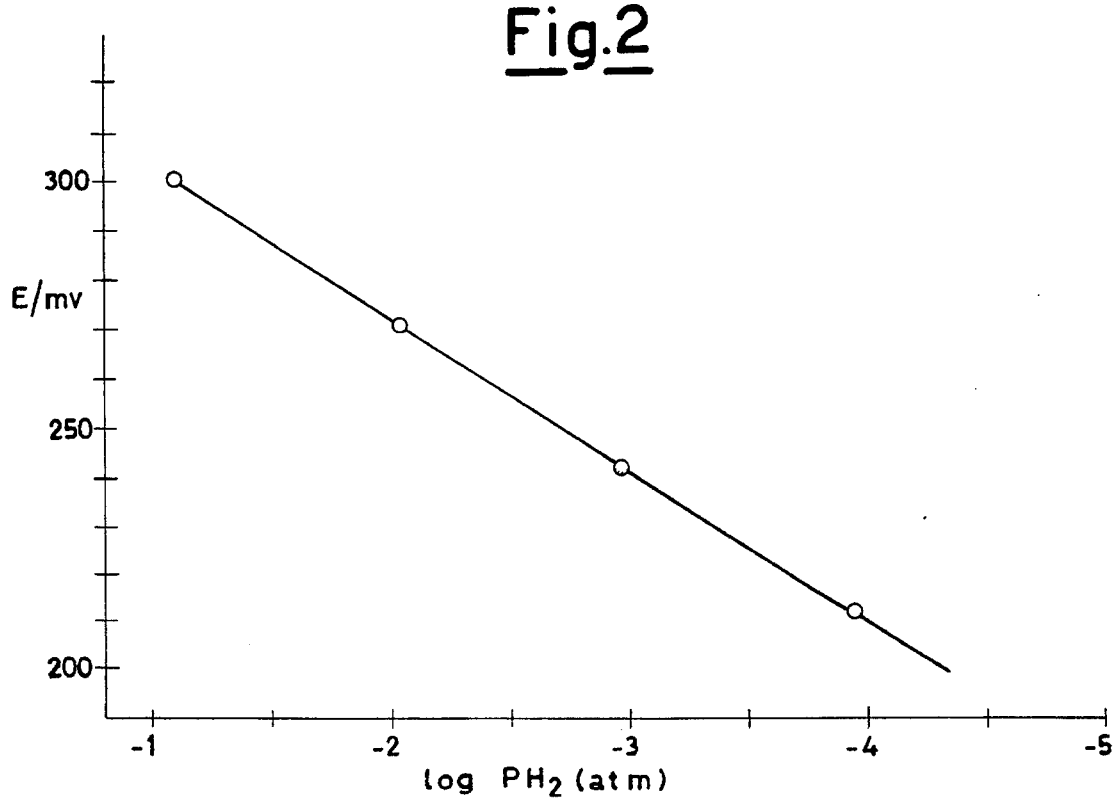
FIG. 2 is a calibration curve for the sensor of Example 1.

A sensor constituted by: titanium hydride/membrane of zirconium hydrogen phosphate/Pt (by sputtering) (thin sheet of Ti having a thickness of 0.025 mm, treated with hydrogen for 4 hours at 500° C.) was used in order to detect the hydrogen content of $N_2/H_2$ mixtures. By using $N_2/H_2$ mixtures of known composition, a calibration curve was obtained. Such a curve, at room temperature, is reported in FIG. 2.

EXAMPLE 2

Figure 3:
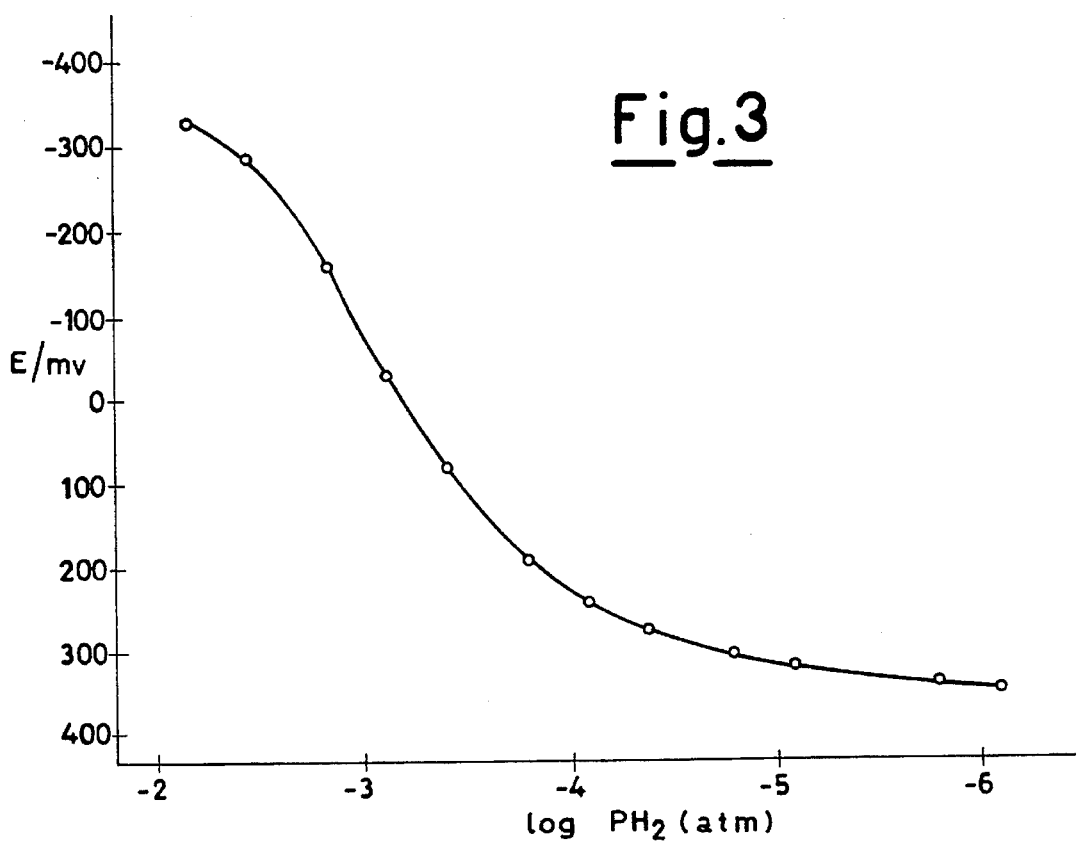
FIG. 3 is a calibration curve of hydrogen in air for the sensor of Example 1.

The sensor of Example 1 was used in order to generate the calibration curve of hydrogen in air. Such a curve, at room temperature, is reported in FIG. 3.

EXAMPLE 3

Figure 4:
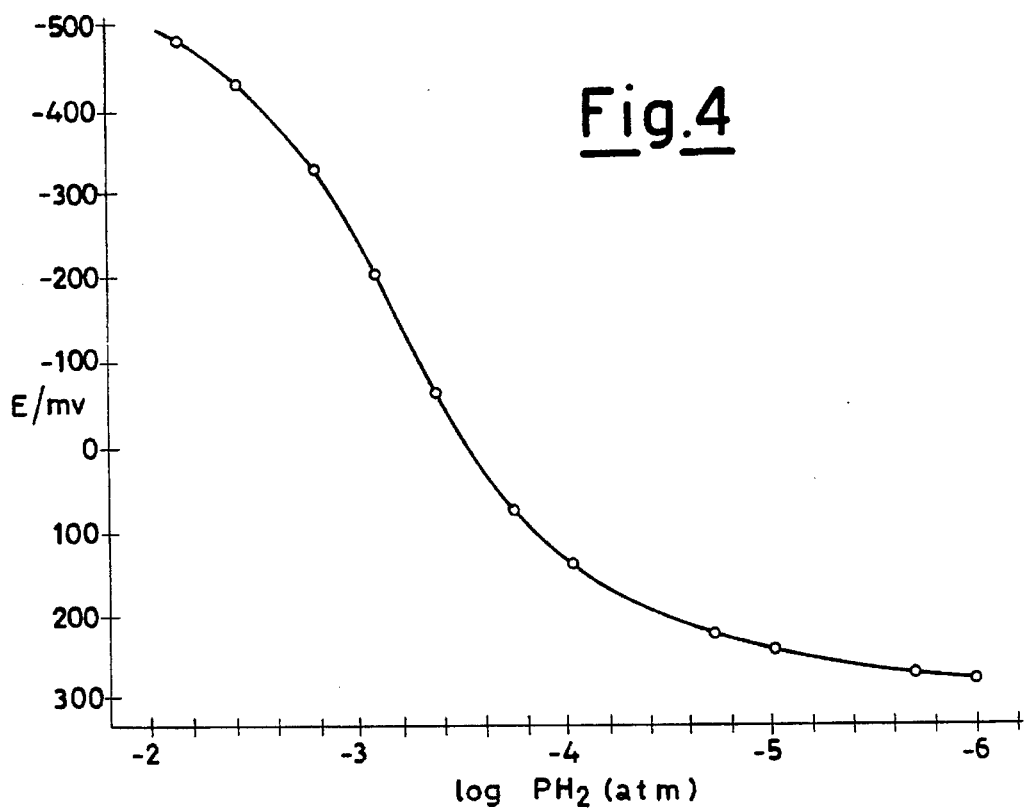
FIG. 4 is a calibration curve for the sensor of Example 3.

A sensor constituted by: titanium hydride/zirconium hydrogen phosphate in film form/Pt (by sputtering) was used in order to detect hydrogen in mixture with air, at room temperature. The relevant calibration curve is shown in FIG. 4.

EXAMPLE 4

A sensor constituted by: zirconium hydride/membrane of zirconium hydrogen phosphate/Pt (by sputtering) (thin sheet of Zr of 0.25 mm of thickness, treated with hydrogen for 8 hours at 500° C.) was used in order to determine hydrogen in the presence of air, at room temperature.

Figure 5:
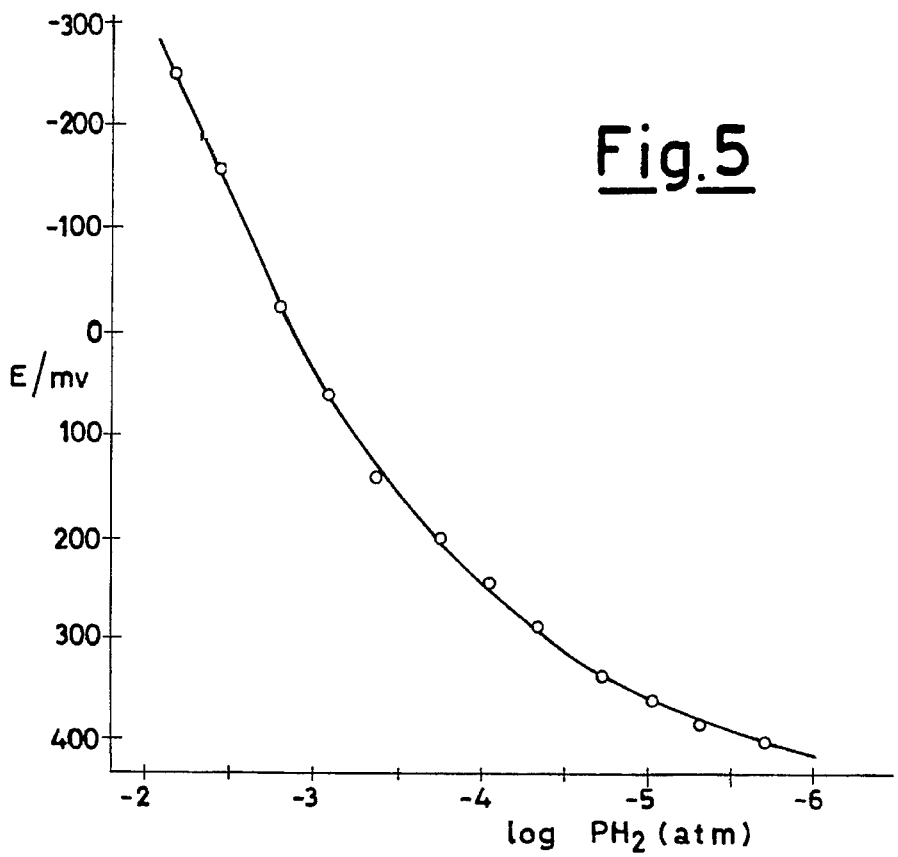
FIG. 5 is a calibration curve for the sensor of Example 4.

The relevant calibration curve is shown in FIG. 5.

EXAMPLE 5

Figure 6:
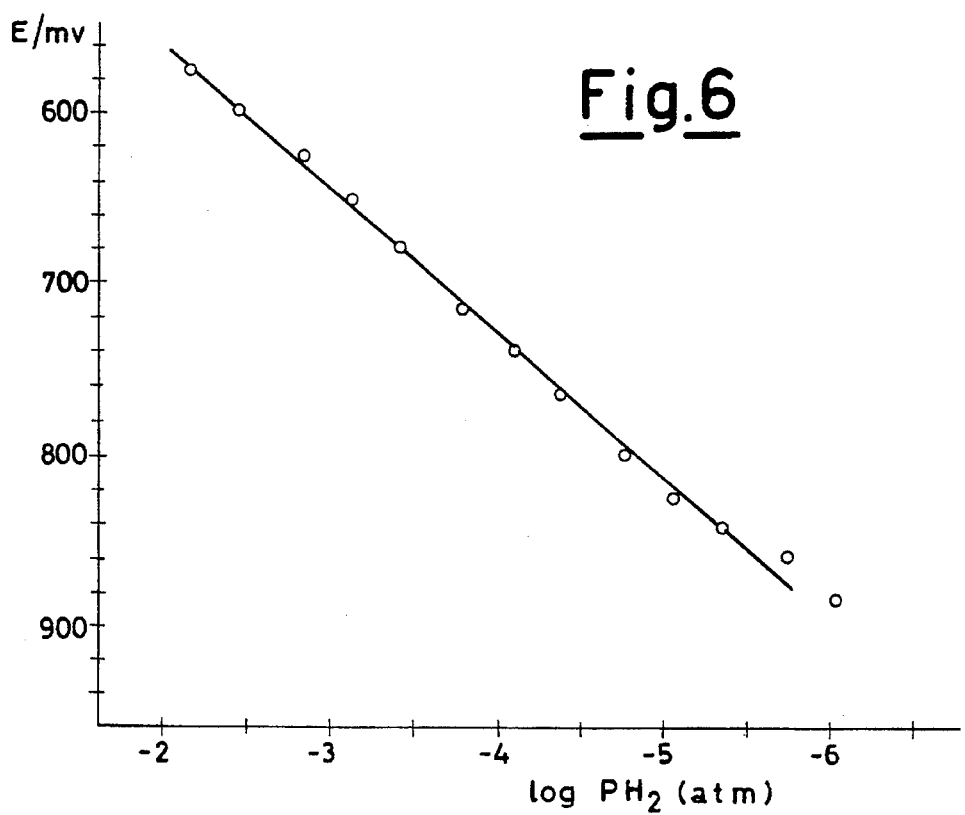
FIG. 6 is a calibration curve for the sensor according to Example 5.

A sensor according to Example 4 was used in order to determine hydrogen, in the presence of air, at 100° C. The relevant calibration curve is shown in FIG. 6.

EXAMPLE 6

Figure 7:
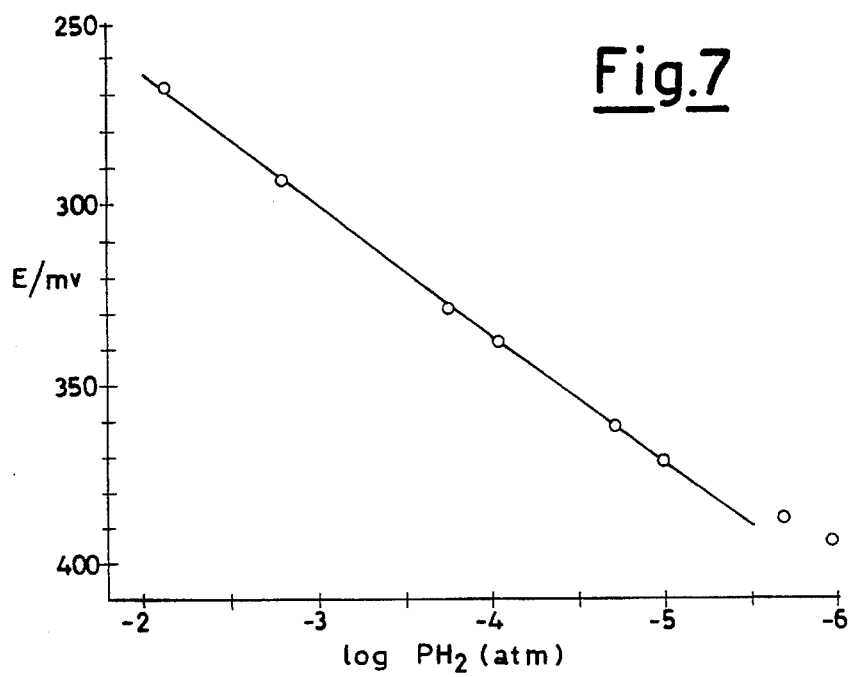
FIG. 7 is a calibration curve for the sensor according to Example 6.

A sensor according to Example 1 was used in order to determine hydrogen, in the presence of air, at 200° C. The relevant calibration curve is shown in FIG. 7.

EXAMPLE 7

A sensor according to Example 1 was used in order to investigate into the interference by carbon monoxide in air at room temperature. It was found that high CO partial pressures, equal to $10^{-3}$ atm, give a slight interference corresponding to a $H_2$ pressure lower than $5.10^{-6}$ atm.

EXAMPLE 8

A reference electrode constituted by $TiH_x$ (prepared at 650° C. under a hydrogen stream for from 3 to 4 hours, and then quickly cooled) was placed into contact with a polymeric organic ion-exchange membrane IONAC MC 3235 (of 0.25 mm of thickness), which was previously converted into the $H^+$ form by means of elution of the $Na^+$ ion with HCl. The free face of said membrane was coated, by means of a sputtering carried out under the same conditions as of the preceding examples, with a thin platinum layer.

Figure 8:
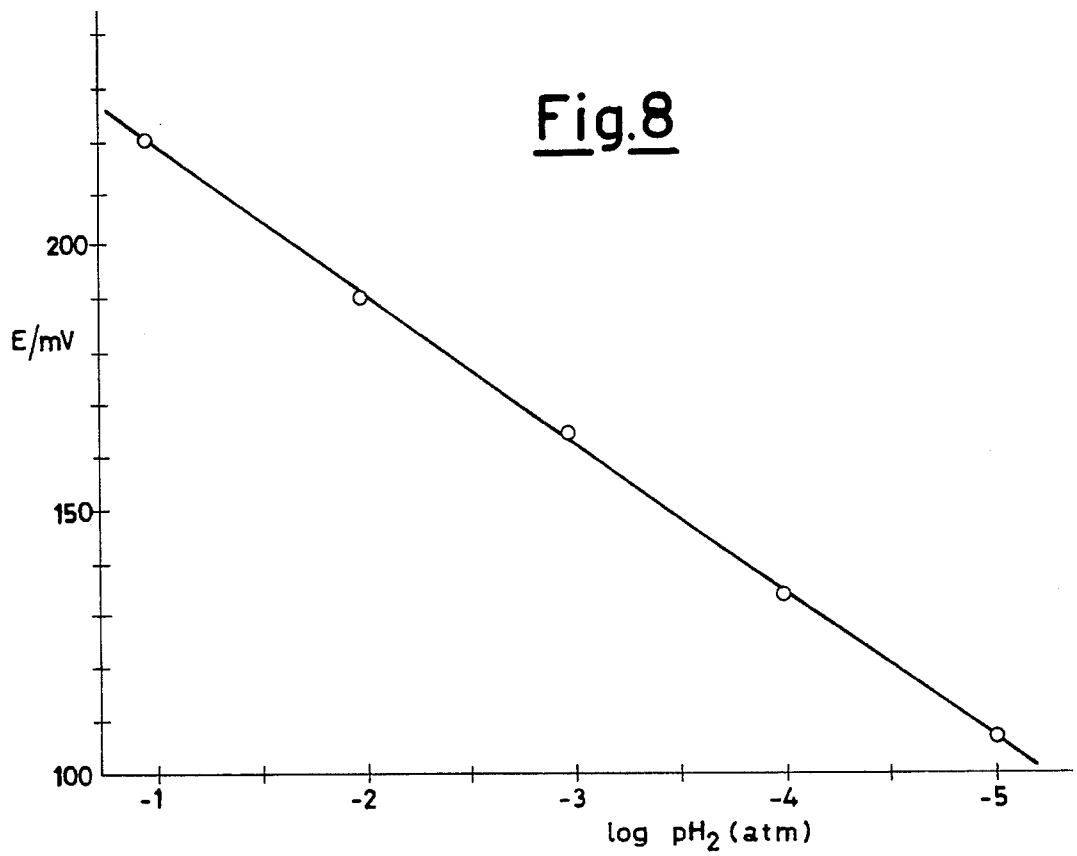
FIG. 8 is a calibration curve of the sensor according to Example 8.

Tests carried out at room temperature with $N_2/H_2$ mixtures (FIG. 8) showed that the e.m,f. of the sensor, in accordance with the Nernst equation, is a linear function of the logarithm of hydrogen partial pressure (28 mV per logarithmic unit).

The speed of response of such a sensor is of the order of 10 seconds.

EXAMPLE 9

A sensor at all similar to the sensor disclosed in the preceding example was prepared by using a commercial NAFION membrane, as the protonic conductor, in $H^+$ form (thickness 0.1 mm). Very good results, at all similar to those as already reported for the polymeric membrane of the preceding example, were obtained.

One should anyway observe that the NAFION membranes resulted to be extremely sensitive to even partial dehydrations, so that special precautions have to be taken in order to keep said membranes constantly damp during the course of the measurement.

In the herein described tests, the gas mixtures under investigation were saturated with water (relative humidity $\geq 90\%$) before being fed to the sensor.

We claim:

1. Solid-state sensor for determining the concentration of hydrogen, comprising a catalyzing electrode and a reference electrode separated by a film or membrane of zirconium hydrogen phosphate having a layer structure of α-type, wherein the reference electrode is a solid-state reference electrode consisting essentially of a metallic hydride selected from the group consisting of zirconium hydride and titanium hydride.

2. Sensor according to claim 1, wherein the protonic conductor comprises a plurality of α-type zirconium hydrogen phosphate layers.

3. Sensor according to claim 1, wherein said zirconium hydrogen phosphate film or membrane layers are obtained from colloidal dispersions of zirconium phosphate. of α-type.

4. Sensor of claim 1 wherein said reference electrode is titanium hydride.

* * * * *